(12) United States Patent
Daphna et al.

(10) Patent No.: US 9,927,632 B2
(45) Date of Patent: *Mar. 27, 2018

(54) HYPER-OSMOTIC EYE CONTACT LENS

(71) Applicants: Ofer Daphna, Beit Elazan (IL); Arie Marcovich, Rehovot (IL); Soheil Shaer, Haifa (IL); Nahum Ferera, Petah Tikva (IL)

(72) Inventors: Ofer Daphna, Beit Elazan (IL); Arie Marcovich, Rehovot (IL); Soheil Shaer, Haifa (IL); Nahum Ferera, Petah Tikva (IL)

(73) Assignee: Eyeyon Medical Ltd., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/814,521

(22) Filed: Jul. 31, 2015

(65) Prior Publication Data

US 2017/0031180 A1    Feb. 2, 2017

Related U.S. Application Data

(63) Continuation of application No. 13/785,157, filed on Mar. 5, 2013, now Pat. No. 9,097,915.

(51) Int. Cl.
*G02C 7/00*    (2006.01)
*G02C 7/04*    (2006.01)
*A61F 9/00*    (2006.01)

(52) U.S. Cl.
CPC ............. *G02C 7/04* (2013.01); *G02C 7/047* (2013.01); *G02C 7/049* (2013.01); *A61F 9/0017* (2013.01); *G02C 2202/06* (2013.01)

(58) Field of Classification Search
CPC ........ G02C 7/045; G02C 7/041; G02C 7/042; G02C 7/043; G02C 7/046; G02C 7/047
USPC ................. 351/159.02, 159.04, 159.34
See application file for complete search history.

(56) References Cited

U.S. PATENT DOCUMENTS

| 5,526,071 | A | * | 6/1996 | Seidner | ........... B29D 11/00086 351/159.41 |
| 6,010,219 | A | * | 1/2000 | Stoyan | ................... G02C 7/047 351/159.23 |
| 2009/0303432 | A1 | * | 12/2009 | Suzuki | ..................... G02C 7/04 351/159.02 |
| 2013/0293832 | A1 | * | 11/2013 | de Juan, Jr. | .............. G02C 7/04 351/159.33 |

FOREIGN PATENT DOCUMENTS

WO    WO 2009078021 A1 *    6/2009    ............... G02C 7/04

* cited by examiner

*Primary Examiner* — Stephone B Allen
*Assistant Examiner* — Travis Fissel
(74) *Attorney, Agent, or Firm* — Dekel Patent Ltd.; David Klein

(57) ABSTRACT

A hyper-osmotic contact lens including a contact lens including a central convex disc, a peripheral curved portion that extends radially from the disc, an annular groove formed in the disc and one or more apertures formed in the groove.

6 Claims, 2 Drawing Sheets

HYPER-OSMOTIC EYE CONTACT LENS

CROSS-REFERENCE TO RELATED APPLICATIONS

This application is a continuation of U.S. patent application Ser. No. 13/785,157, filed Mar. 5, 2013, now U.S. Pat. No. 9,097,915, which is incorporated herein by reference.

FIELD OF THE INVENTION

The present invention relates generally to contact lenses and in particular to contact lenses designed to compensate for an over-hydrated, edematous cornea.

BACKGROUND OF THE INVENTION

U.S. Pat. No. 8,096,655 to Daphna describes a hyper-osmotic contact lens designed to treat corneal edema. The hyper-osmotic contact lens absorbs fluid from an edematous cornea by the force of an osmotic gradient. The hyper-osmotic contact lens is designed as a microcontainer with walls that are thin relative to its general dimensions, and is shaped as a lens with anterior and posterior walls, which define and bound a hyper-osmotic chamber. The posterior wall, which is the area in which the cornea and the contact lens overlap, is made of a selective water permeable membrane. In this area, water from the edematous cornea can flow out of the cornea into the hyper-osmotic chamber by the force of osmosis, thus dehydrating the cornea itself. The hyper-osmotic chamber may contain a hyper-osmotic transparent medium such as dry hydrogel or solution such as glycerol, salts, etc.

SUMMARY OF THE INVENTION

The present invention relates to a hyper-osmotic contact lens, which provides structure different than U.S. Pat. No. 8,096,655, as is described further in detail hereinbelow.

The hyper-osmotic contact lens is designed to treat corneal edema. The hyper-osmotic contact lens absorbs fluid from an edematous cornea by the force of an osmotic gradient. The refractive property of the lens can be taken into account according to patient refraction.

There is provided in accordance with an embodiment of the present invention a contact lens including a contact lens including a central convex disc, a peripheral curved portion that extends radially from the disc, an annular groove formed at an interior junction of the disc and the peripheral curved portion, and one or more apertures formed in the groove.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
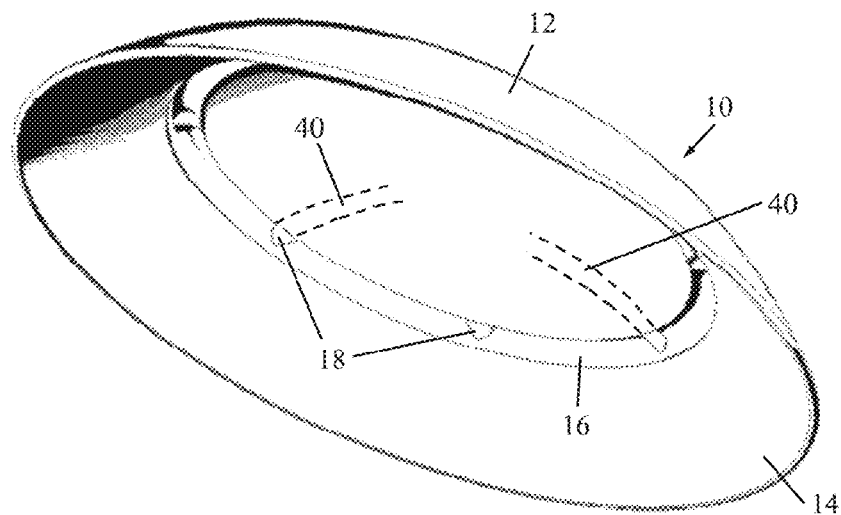
FIG. 1 is a simplified front view illustration of a hyper-osmotic eye contact lens, constructed and operative in accordance with an embodiment of the present invention.

Reference is now made to FIG. 1, which illustrates a hyper-osmotic eye contact lens 10, constructed and operative in accordance with an embodiment of the present invention.

Contact lens 10 includes a central convex disc 12 from which radially extends a peripheral curved portion 14. Central convex disc 12 and peripheral curved portion 14 can have the same curvature or different curvatures. An annular groove 16 is formed at the interior (i.e., posterior side) junction of disc 12 and peripheral curved portion 14. One or more apertures (through holes) 18 may be formed in groove 16. In one embodiment, there are 6 apertures 18; in another embodiment there are 8 apertures 18, but the invention is not limited to these numbers.

Central convex disc 12 is made of a material that is oxygen permeable and dimensionally stable for use as a contact lens. A preferred example is G4X p-GMA/HEMA (hioxifilcon D), with water content in the range of approximately 50-75%, commercially available from Benz Research & Development, Sarasota, Fla., US. The invention is not limited to this material.

In one embodiment, the inner volume of lens 10, preferably that of central convex disc 12, defines a reservoir (hyper-osmotic chamber) 20 (FIG. 2) for supporting therein a hyper-osmotic substance 22 (FIG. 4), which may be a hyper-osmotic transparent medium such as, but not limited to, dry hydrogel, etc., or solution such as, but not limited to, glycerol, salt solution, etc. Substance 22 may also have suitable refraction and transparency properties, which may be selected for modifying vision of a patient.

The presence of hyper-osmotic substance 22 creates a molecular concentration gradient and thus osmotic pressure gradient between the cornea and hyper-osmotic chamber 20. The osmotic pressure gradient results in a net flow of fluid from the cornea directly into hyper-osmotic chamber 20 by osmosis, thus dehydrating the cornea. Lens 10 can be constructed to reach a steady state net fluid flow or not to reach steady state.

Lens 10 has a suitable volume to enable functioning for a sufficient duration until it is full. Accordingly, contact lens 10 may be used for daily treatment, partial daily treatment or overnight treatment, or any other treatment period which is needed for the patient treatment when it is mounted upon a cornea in an edematous state. Contact lens 10 may be sized to fit over the cornea to the limbus, or alternatively may extend over the limbus.

In another embodiment, chamber 20 is not filled with any substance 22, but instead simply fits over the cornea or cornea and limbus or beyond the limbus. It has been found that the chamber 20 defined by central convex disc 12, even when initially empty (that is, devoid of a hyper-osmotic substance, but, for example, containing air), can create an osmotic pressure gradient that results in a net flow of fluid from the cornea directly into hyper-osmotic chamber 20 by osmosis, thus dehydrating the cornea. A tear film is created, due to the osmotic pressure gradient, between the lens 10 and the cornea. Due to the groove 16 and apertures 18, the tear film creates a surface tension underneath the lens 10 which is relatively trapped and slow to escape. (The apertures 18 are small so the drops do not flow past them but instead are trapped due to surface tension). The entrapped salty tear film increases the hyper-osmotic pressure, which synergistically increases dehydration of the cornea. The structure of the apertures and lens is such that any liquid drop that placed on the exterior surface of the lens will be drawn through the relatively unidirectional apertures 18 to the interior of the lens. Thus the lens serves as a trap for fluids, such as a hypertonic solution or any other drug.

Optionally, the lens 10 can be heavier at its bottom portion, which may increase the stability of the lens against any torsional movement and maintain the lens in place.

Figure 2:
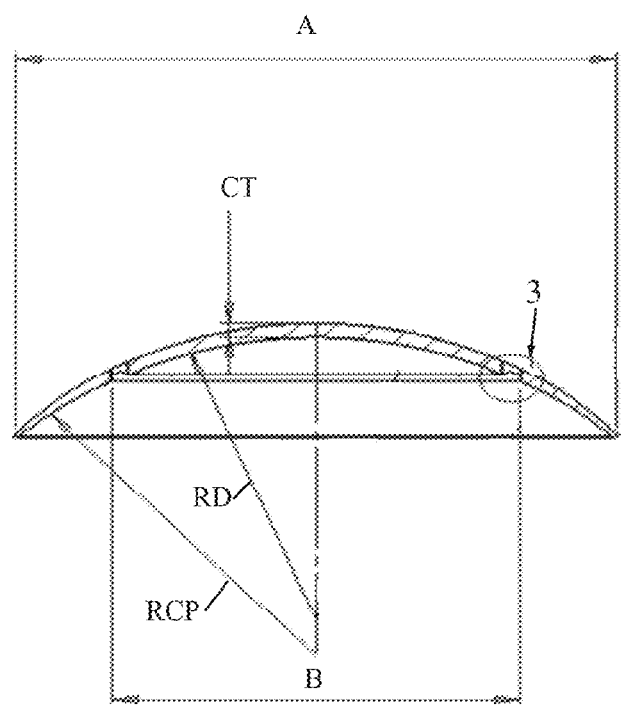
FIG. 2 is a cross sectional view of the hyper-osmotic eye contact lens.
Figure 4:
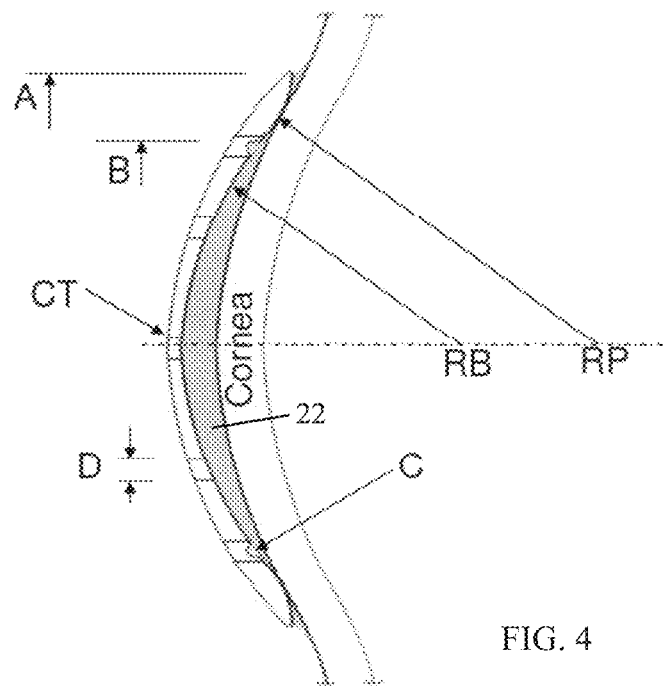
FIG. 4 is a simplified side view of the hyper-osmotic eye contact lens mounted on an eye, in accordance with an embodiment of the present invention.

Reference is now made to FIGS. 2 and 4. Non-limiting, exemplary values of lens dimensions are now described.

Figure 3:
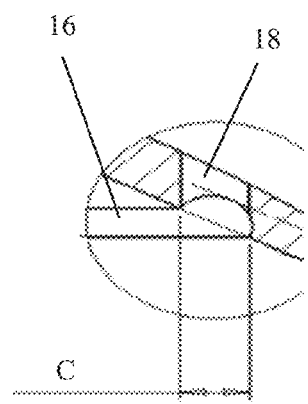
FIG. 3 is an enlarged cross-section of a hole and annular groove of the lens.

In one embodiment of the invention, the parameters are as follows:
 A overall lens diameter (including peripheral curved portion 14)=11.50 mm
 D diameter of aperture 18=0.5 mm
 B reservoir diameter (diameter of hyper-osmotic chamber 20)=7.50 mm
 C thickness of annular groove 16=0.40 mm
 CT center thickness=0.4 mm (see FIG. 3)
 RP peripheral eye radius
 RB reservoir radius is 0.3 mm steeper than central eye flat meridian
 RD radius (curvature) of central convex disc 12=8.60 mm
 RCP radius (curvature) of peripheral curved portion 14=8.60 mm In another embodiment of the invention, the parameters are as follows:
 A overall lens diameter (including peripheral curved portion 14)=15.00 mm
 D diameter of aperture 18=1.50 mm
 B reservoir diameter (diameter of hyper-osmotic chamber 20)=9.50 mm
 C thickness of annular groove 16=0.40 mm
 CT center thickness=0.25 mm
 RP peripheral eye radius
 RB reservoir radius is 0.3 mm steeper than central eye flat meridian
 RD radius (curvature) of central convex disc 12=7.80 mm
 RCP radius (curvature) of peripheral curved portion 14=9.60 mm In still another embodiment of the invention, the parameters are as follows:
 A overall lens diameter (including peripheral curved portion 14)=14.00 mm
 D diameter of aperture 18=0.5 mm
 B reservoir diameter (diameter of hyper-osmotic chamber 20)=9.50 mm
 C thickness of annular groove 16=0.40 mm
 CT center thickness=0.4 mm
 RP peripheral eye radius
 RB reservoir radius is 0.3 mm steeper than central eye flat meridian
 RD radius (curvature) of central convex disc 12=8.60 mm
 RCP radius (curvature) of peripheral curved portion 14=8.60 mm In yet another embodiment of the invention, the parameters are as follows:
 A overall lens diameter (including peripheral curved portion 14)=11.00 mm
 D diameter of aperture 18=0.5 mm
 B reservoir diameter (diameter of hyper-osmotic chamber 20)=7.50 mm
 C thickness of annular groove 16=0.30 mm
 CT center thickness=0.4 mm
 RP peripheral eye radius
 RB reservoir radius is 0.3 mm steeper than central eye flat meridian
 RD radius (curvature) of central convex disc 12=8.60 mm
 RCP radius (curvature) of peripheral curved portion 14=8.80 mm It is noted that in the first and fourth examples, the lens basically covers just the cornea, whereas in the second and third embodiments the lens extends to the limbus and beyond.

As shown in broken lines in FIG. 1, as another option one or more arcuate grooves 40 may be formed at least partially in the spherical longitudinal direction across the inner surface of central convex disc 12. Grooves 40 may extend from apertures 18.

Figure 5:
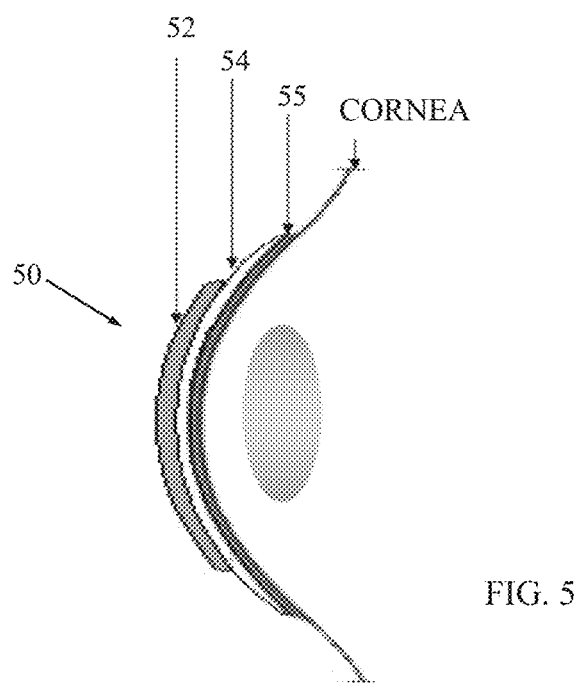
FIG. 5 is a simplified side view of a hyper-osmotic eye contact lens mounted on an eye, in accordance with another embodiment of the present invention.

Reference is now made to FIG. 5, which illustrates a hyper-osmotic eye contact lens 50, constructed and operative in accordance with another embodiment of the present invention.

Contact lens 50 includes an anterior lens 52 that is mounted over a posterior lens 54, which in turn is mounted on the cornea C of the eye. A tear film 55 may be present between posterior lens 54 and the cornea. Without limitation, anterior lens 52 and posterior lens 54 may be made of G4X p-GMA/HEMA (hioxifilcon D), respectively with 73% and 54% water content. Dimensions of anterior lens 52 may be similar to the first above example, whereas posterior lens 54 may be similar to the second above example. The invention is not limited to these values.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A method for creating an osmotic pressure gradient that results in a net flow of fluid from a cornea, comprising:
 placing a contact lens over a cornea of an eye, the contact lens comprising:
  a central convex disc;
  a peripheral curved portion that extends radially from said disc;
  an annular groove formed in said disc; and
  one or more apertures formed in said groove, wherein an inner volume of said lens defines a chamber which is initially devoid of a hyper-osmotic substance;
 and wherein said chamber over time creates an osmotic pressure gradient between the cornea and said chamber that results in a net flow of fluid from the cornea directly into said chamber by osmosis, thus dehydrating the cornea;
 and wherein the osmotic pressure gradient creates a tear film between said contact lens and the cornea and due to said groove and said apertures, said tear film creates a surface tension underneath said contact lens.

2. The method according to claim 1, wherein said apertures are sufficiently small so that said tear film does not flow out of said contact lens past said apertures.

3. The method according to claim 1, wherein said tear film increases hyper-osmotic pressure in said chamber.

4. The method according to claim 1, wherein said apertures are sized such that a liquid drop placed on an exterior surface of said contact lens is drawn through said apertures to an interior of said contact lens.

5. The method according to claim 1, wherein said chamber extends over the cornea and at least a portion of a limbus.

6. The method according to claim 1, wherein said chamber extends beyond a limbus.

* * * * *